(12) United States Patent
McGrath et al.

(10) Patent No.: US 8,119,394 B2
(45) Date of Patent: *Feb. 21, 2012

(54) CELL CULTURE DEVICES HAVING ULTRATHIN POROUS MEMBRANE AND USES THEREOF

(75) Inventors: James L. McGrath, Fairport, NY (US); Thomas R. Gaborski, Pittsford, NY (US); Christopher C. Striemer, Rochester, NY (US); Philippe M. Fauchet, Pittsford, NY (US)

(73) Assignee: University of Rochester, Rochester, NY (US)

( * ) Notice: Subject to any disclaimer, the term of this patent is extended or adjusted under 35 U.S.C. 154(b) by 1301 days.

This patent is subject to a terminal disclaimer.

(21) Appl. No.: 11/686,196

(22) Filed: Mar. 14, 2007

(65) Prior Publication Data

US 2007/0231887 A1   Oct. 4, 2007

Related U.S. Application Data

(60) Provisional application No. 60/782,205, filed on Mar. 14, 2006.

(51) Int. Cl.
*C12M 3/06* (2006.01)
*C12M 1/34* (2006.01)

(52) U.S. Cl. .... 435/297.1; 435/30; 435/401; 435/288.5; 435/288.7; 435/297.5

(58) Field of Classification Search .............. 435/297.5, 435/297.1
See application file for complete search history.

(56) References Cited

U.S. PATENT DOCUMENTS

| | | | |
|---|---|---|---|
| 4,191,182 A | 3/1980 | Popovich et al. |
| 4,329,157 A | 5/1982 | Dobo et al. |
| 4,557,995 A | 12/1985 | Broers et al. |
| 4,784,721 A | 11/1988 | Holmen et al. |
| 4,824,568 A | 4/1989 | Allegrezza, Jr. et al. |
| 5,334,314 A | 8/1994 | Neel et al. |
| 5,354,695 A | 10/1994 | Leedy |
| 5,413,679 A | 5/1995 | Godbey |
| 5,503,657 A | 4/1996 | Bouard et al. |
| 5,552,046 A | 9/1996 | Johnston et al. |
| 5,567,302 A | 10/1996 | Song et al. |
| 5,595,646 A | 1/1997 | Foos et al. |
| 5,750,329 A | 5/1998 | Quinn et al. |
| 5,753,014 A | 5/1998 | Van Rijn |
| 5,763,275 A | 6/1998 | Nagels et al. |
| 5,904,545 A | 5/1999 | Smith et al. |

(Continued)

FOREIGN PATENT DOCUMENTS

DE    10353894 A1    2/2005

(Continued)

OTHER PUBLICATIONS

International Search Report for corresponding PCT Application US07/64001, May 22, 2008.

(Continued)

*Primary Examiner* — William H Beisner
(74) *Attorney, Agent, or Firm* — LeClairRyan, a Professional Corporation (57) ABSTRACT

Disclosed is a device for co-culturing two or more populations of cells using ultrathin, porous membranes positioned between cell culture chambers. Multiple chamber devices and uses thereof are described, including the formation of in vitro tissue models for studying drug delivery, cell-cell interactions, and the activity of low abundance molecular species.

51 Claims, 7 Drawing Sheets

U.S. PATENT DOCUMENTS

| | | | |
|---|---|---|---|
| 5,948,470 A | 9/1999 | Harrison et al. | |
| 6,017,773 A | 1/2000 | Fauchet et al. | |
| 6,039,877 A | 3/2000 | Chevallet et al. | |
| 6,120,875 A | 9/2000 | Haumont et al. | |
| 6,332,914 B1 | 12/2001 | Lee | |
| 6,399,234 B2 | 6/2002 | Bonk et al. | |
| 6,406,605 B1 | 6/2002 | Moles | |
| 6,454,938 B2 | 9/2002 | Moon et al. | |
| 6,517,994 B2 | 2/2003 | Watanabe | |
| 6,780,786 B2 | 8/2004 | Dougherty | |
| 6,803,581 B2 | 10/2004 | Prince et al. | |
| 6,811,037 B2 | 11/2004 | Hintsche | |
| 6,899,744 B2 | 5/2005 | Mundschau | |
| 6,946,015 B2 | 9/2005 | Jorgensen et al. | |
| 7,112,287 B2 | 9/2006 | Yagi et al. | |
| 7,141,096 B2 | 11/2006 | Carboneri et al. | |
| 7,282,148 B2 | 10/2007 | Dalton et al. | |
| 7,393,392 B2 | 7/2008 | Yamaguchi et al. | |
| 7,410,531 B2 | 8/2008 | Edlund et al. | |
| 7,425,231 B2 | 9/2008 | Carolan et al. | |
| 7,485,233 B2 | 2/2009 | Vane et al. | |
| 7,662,218 B2 | 2/2010 | Maeda et al. | |
| 7,922,795 B2 * | 4/2011 | Striemer et al. | 96/4 |
| 2002/0192680 A1 * | 12/2002 | Chan et al. | 435/6 |
| 2003/0096424 A1 | 5/2003 | Mao et al. | |
| 2003/0162399 A1 | 8/2003 | Singh | |
| 2003/0183080 A1 | 10/2003 | Mundschau | |
| 2003/0205138 A1 | 11/2003 | Edlund et al. | |
| 2003/0217966 A1 | 11/2003 | Tapsak et al. | |
| 2003/0222012 A1 | 12/2003 | Lee et al. | |
| 2003/0222015 A1 | 12/2003 | Oyama et al. | |
| 2004/0035782 A1 | 2/2004 | Muller | |
| 2004/0063322 A1 | 4/2004 | Yang | |
| 2004/0067546 A1 * | 4/2004 | Leng et al. | 435/30 |
| 2004/0129135 A1 | 7/2004 | Roark et al. | |
| 2004/0154641 A1 | 8/2004 | Montierth | |
| 2004/0187558 A1 | 9/2004 | Dye et al. | |
| 2004/0244591 A1 | 12/2004 | Edlund et al. | |
| 2004/0245191 A1 | 12/2004 | Yagi et al. | |
| 2005/0082641 A1 | 4/2005 | Leedy | |
| 2005/0084792 A1 | 4/2005 | Yokoi et al. | |
| 2005/0092676 A1 | 5/2005 | Dalton et al. | |
| 2005/0188843 A1 | 9/2005 | Edlund et al. | |
| 2005/0229786 A1 | 10/2005 | Wetzig | |
| 2005/0241477 A1 | 11/2005 | Mundschau et al. | |
| 2005/0242022 A1 | 11/2005 | Kang et al. | |
| 2005/0268782 A1 | 12/2005 | Kulkarni et al. | |
| 2005/0284814 A1 | 12/2005 | Mairal et al. | |
| 2006/0012086 A1 | 1/2006 | Munch-Laursen et al. | |
| 2006/0016332 A1 | 1/2006 | Ma et al. | |
| 2006/0049101 A1 | 3/2006 | Suib et al. | |
| 2006/0108714 A1 | 5/2006 | Pedersen et al. | |
| 2006/0154361 A1 * | 7/2006 | Wikswo et al. | 435/289.1 |
| 2006/0173259 A1 | 8/2006 | Flaherty et al. | |
| 2006/0175249 A1 | 8/2006 | Vane et al. | |
| 2006/0213368 A1 | 9/2006 | Kita et al. | |
| 2006/0230937 A1 | 10/2006 | Smirnov et al. | |
| 2006/0231484 A1 | 10/2006 | Haring et al. | |
| 2006/0231485 A1 | 10/2006 | Yoshinaga et al. | |
| 2006/0237360 A1 | 10/2006 | Mizuno et al. | |
| 2006/0243655 A1 | 11/2006 | Striemer et al. | |
| 2006/0273004 A1 | 12/2006 | Kang et al. | |
| 2006/0278580 A1 | 12/2006 | Striemer et al. | |
| 2006/0289351 A1 | 12/2006 | Xiao et al. | |
| 2007/0026392 A1 | 2/2007 | Warren et al. | |
| 2007/0029256 A1 | 2/2007 | Nakano et al. | |
| 2007/0039471 A1 | 2/2007 | Hofmann | |
| 2007/0079703 A1 | 4/2007 | Carolan et al. | |
| 2007/0163437 A1 | 7/2007 | Ikeda et al. | |
| 2008/0178736 A1 | 7/2008 | Carolan et al. | |
| 2008/0245735 A1 | 10/2008 | Hennige et al. | |

FOREIGN PATENT DOCUMENTS

| | | |
|---|---|---|
| EP | 1611941 A2 | 4/2006 |
| WO | 2004/020341 A2 | 3/2004 |
| WO | 2005/007276 A1 | 1/2005 |
| WO | WO 2006/119251 A2 | 11/2006 |
| WO | WO 2006/119252 A2 | 11/2006 |
| WO | 2007/021919 A1 | 2/2007 |

OTHER PUBLICATIONS

Reisman et al., "The Controlled Etching of Silicon in Catalyzed Ethylenediamine-Pyrocatechol-Water Solutions," *J. Electrochem. Soc.* 126(8):1406-1415 (1979).

Grom et al., "Ordering and Self-Organization in Nanocrystalline Silicon," *Nature* 407:358-361 (2000).

Chen et al., "Enhancement of Electron Mobility in Nanocrystalline Silicon/Crystalline Silicon Heterostructures," *J. Applied Phys.* 97(024305):1-5 (2004).

Chen et al., "Large On-off Ratios and Negative Differential Resistance in a Molecular Electronic Device," *Science* 286:1550-1552 (1999).

Jirage et al., "Nanotubule-based Molecular-filtration Membranes," *Science* 278:655-658 (1997).

Ko et al., "A Polymer-based Microfluidic Device for Immunosensing Biochips," *Lab Chip* 3:106-113 (2003).

Környei et al., "Humoral and Contact Interactions in Astroglia/Stem Cell Co-cultures in the Course of Glia-Induced Neurogenesis," *GLIA* 49:430-444 (2005).

Kuo et al., "Hybrid Three-dimensional Nanofluidic/Microfluidic Devices Using Molecular Gates," *Sensors and Actuators A* 102:223-233 (2003).

Lee et al., "Antibody-Based Bio-Nanotube Membranes for Enantiomeric Drug Separations," *Science* 296:2198-2200 (2002).

Létant et al., "Functionalized Silicon Membranes for Selective Bio-organism Capture," *Nat. Mater.* 2:391-395, suppl'y inform. 1 (2003).

Li et al., "Ion-beam Sculpting at Nanometre Length Scales," *Nature* 412:166-169 (2001).

Liao et al., "Use of Electrochemical DNA Biosensors for Rapid Molecular Identification of Uropathogens in Clinical Urine Specimens," *J. Clin. Microbiol.* 44(2) 561-570 (2006).

Midwood et al., "Easy and Efficient Bonding of Biomolecules to an Oxide Surface of Silicon," *Langmuir* 20:5501-5505 (2004).

Ma et al., "An Endothelial and Astrocyte Co-culture Model of the Blood-brain Barrier Utilizing an Ultra-thin, Nanofabricated Silicon Nitride Membrane," Lab Chip 5:74-85 (2005).

Schmuhl et al., "Si-compatible Ion Selective Oxide Interconnects with High Tunability," *Adv. Mater.* 16(11):900-904 (2004).

Storm et al., "Fabrication of Solid-state Nanopores with Single-nanometre Precision," *Nat. Mater.* 2:537-540 (2003) with online supplemental information attached.

Striemer, "Applications of Silicon Nanostructures Compatible with Existing Manufacturing Technology," University of Rochester, Department of Electrical and Computer Engineering 1-136 (2004).

Striemer et al., "Charge- and Size-based Separation of Macromolecules Using Ultrathin Silicon Membranes," *Nature* 445(7129):749-53 (2007) with online supplemental information attached.

Tong et al., "Silicon Nitride Nanosieve Membrane," *Nano Lett.* 4(2):283-287 (2004).

Search report dated Aug. 16, 2011 for corresponding European application No. 07758546.1.

\* cited by examiner

CELL CULTURE DEVICES HAVING ULTRATHIN POROUS MEMBRANE AND USES THEREOF

This application claims the priority benefit of provisional U.S. Patent Application Ser. No. 60/782,205, filed Mar. 14, 2006, which is hereby incorporated by reference in its entirety.

FIELD OF THE INVENTION

The present invention is directed to ultrathin nanoporous silicon membranes for use in biological culture devices, and uses thereof.

BACKGROUND OF THE INVENTION

Ultra-thin membranes can be used for a wide variety of applications including use as nanosieves and nano-filters. Tong et al., "Silicon Nitride Nanoseive Membrane," *Nano Lett* 4:283-287 (2004); Lee et al., "Antibody-Based Bio-Nanotube Membranes for Enantiomeric Drug Separations," *Science* 296:2198-2200 (2002). Membranes can also be used for biological co-cultures, however, current methods of biological co-culturing employ relatively thick membranes, on the order of several hundred nanometers, having relatively large pores, also on the order of several hundred nanometers in diameter. In some instances, prior art silicon nitride membranes require the deposition of collagen. Ma et al., "An Endothelial and Astrocyte Co-culture Model of the Blood-brain Barrier Utilizing an Ultra-thin, Nanofabricated Silicon Nitride Membrane," *Lab on a Chip* 5:74-85 (2005).

There is a need for a culture device that allows for tighter control of cellular contact and molecular interaction across the membrane. Specifically, in some instances it would be desirable to obtain a culturing device that can promote or restrict cell-to-cell contact, promote or restrict transfer of signaling molecules across the membrane, restrict signaling molecules based on size, restrict signaling molecules based on their charge, detect low abundance molecular species, and/or allow for imaging of cells on either side of the membrane.

The present invention is directed to overcoming these and other deficiencies in the art.

SUMMARY OF THE INVENTION

A first aspect of the present invention relates to a cell culture device for culturing one or more populations of cells. The device includes: first and second chambers separated by at least one nanoscale membrane positioned between the first and second chambers, the at least one nanoscale membrane having an average thickness of less than about 100 nm, and having a plurality of pores extending between opposite sides thereof.

A second aspect of the present invention relates to a sterile package that includes a sealed package defining an interior that is sterile, and a device according to the first aspect of the present invention positioned within the interior of the sealed package.

A third aspect of the present invention relates to a kit that includes the device according to the first aspect of the present invention and one or more of the following components: (i) a cell culture medium, (ii) one or more cell lines, and (iii) instructions for culturing one or more cells.

A fourth aspect of the present invention relates to a method of co-culturing two or more populations of cells. This method includes the steps of: providing a device according to the first aspect of the present invention; and culturing a first population of cells in the first chamber and a second population of cells in the second chamber (i.e., on opposite sides of the nanoscale membrane).

A fifth aspect of the present invention relates to a method of visualizing cells. This method includes the steps of: providing a cell culture device according to the first aspect of the present invention, with cells in the first and/or second chambers; and observing the cells of the first and/or second chambers via microscopy. The nanoscale membranes are optically transparent using various forms of light and electron microscopy.

A sixth aspect of the present invention relates to a method of monitoring low abundance molecular species. This method includes the steps of: providing a cell culture device according to the first aspect of the present invention with cells in the first chamber; and detecting the presence of low abundance molecular species in the second chamber.

A seventh aspect of the present invention relates to an in vitro tissue that includes: two cell types segregated on opposite sides of a nanoscale membrane having an average thickness of less than about 100 nm, and having a plurality of pores extending between opposite sides thereof. The two cell types are capable of cell-to-cell contact across the membrane and/or small molecule-mediated cell-to-cell communication.

An eighth aspect of the present invention relates to an in vitro tissue that includes: at least three cell types segregated on opposite sides of at least two nanoscale membranes that each have an average thickness of less than about 100 nm and a plurality of pores extending between opposite sides thereof. One membrane segregates two cell types and another membrane segregates a third cell type from the other cell types. The segregated cells types are capable of cell-to-cell contact across membranes and/or small molecule-mediated cell-to-cell communication.

A ninth aspect of the present invention relates to a method of measuring drug delivery rates through a substantially confluent cell layer. This method includes the steps of: providing a device according to the first aspect of the present invention with a first cell type grown substantially to confluence over the surface of the at least one nanoscale membrane that is exposed to the first chamber; introducing a drug into the first chamber; and determining a drug delivery rate for delivery of the drug through the substantially confluent cell layer of the first chamber and into the second chamber.

A tenth aspect of the present invention relates to an in vitro tissue model that includes: a free-standing, porous membrane that is less than 100 nm in thickness, the membrane having a configuration that defines an internal surface of the membrane and an external surface of the membrane; a first cell type growing on at least a portion of the internal surface of the membrane; and a second cell type growing on at least a portion of the external surface of the membrane. Important embodiments of this aspect of the invention include models for vascular tissue, which include endothelial cells on the internal surface and vascular smooth muscle cells on the external surface, and for nerve guides or prosthetics, which include nerve cells on the internal surface and astrocytes on the external surface.

The cell culture devices of the present invention offer greater control of the degree and type of cellular communication between cell types cultured together. Moreover, because cells are capable of communicating while being maintained in segregated environments, the culture devices allow for the harvesting of substantially pure cell populations, e.g., that have matured or grown or differentiated in a desired manner prior to harvesting. As a consequence, the present invention allows for the growth of a number in vitro tissues that can accurately replicate the native tissue structure. Further, the membranes used in the culture devices of the present invention allow for the detection of the secretion and transport of low abundance molecular species, and the visualization of cells grown on one or both sides of the membrane.

BRIEF DESCRIPTION OF THE DRAWINGS

In FIG. 1A, each upper chamber communicates through the porous membrane with a common lower chamber. In FIG. 1B, each upper chamber communicates with a single lower chamber, and there is no communication between adjacent sets of chambers.

In FIG. 2A, a pair of membranes is used to separate the first and second compartments. Spacers are provided between the membranes so as to preclude cell to cell contact but allow cell signaling. In FIG. 2B, a pair of membranes is used to form first, second, and third compartments. Larger spacers separate the membranes to create an intermediate chamber of a suitable dimension to retain cells. In FIG. 2C, three membranes are used to separate four culture chambers. The embodiments shown in FIGS. 2B-C create multi-layered cell cultures that can be used to imitate more complex tissue interactions.

FIG. 3 illustrates the construction of a multi-well substrate that can be used to form multi-well culture devices. Through simple photolithography techniques as described in co-pending U.S. patent application Ser. No. 11/414,991 to Striemer et al., multiple wells can be created in a single substrate with each well having its own porous membrane. The porous membranes of all wells can be substantially the same (created under substantially identical conditions) or different. Single cells or small colonies can be deposited in each well. The bottoms of the wells can all be exposed to a single, shared chamber or reservoir as shown in FIG. 1A, or each can have a separate small reservoir as shown in FIG. 1B.

FIG. 4A shows a thin membrane with small pores that will exclude cell protrusions but allow cell signaling through small molecule diffusion. FIG. 4B shows a thin membrane with large pores that will enable both cell-cell contact and diffusion of small molecules. FIG. 4C shows cell protrusions that can contact through relatively thick membranes with large pores, but small molecule signaling may be diminished due to the long diffusion distance or binding at the membrane surface.

FIG. 6 illustrates the use of the membranes as sensors. Low abundance molecules can diffuse through the membrane and bind to receptor molecules linked to the opposite side of the membrane. Detection of the diffusible molecule can be achieved using a number of detection strategies.

DETAILED DESCRIPTION OF THE INVENTION

The present invention relates to a device for culturing one or more populations of cells, and various uses thereof.

The culture device of the present invention contains at least two chambers separated by at least one nanoscale membrane. The membrane is positioned between the chambers, has an average thickness of less than about 100 nm, and has a plurality of pores extending between the opposite sides of the membrane.

The chambers can be formed by any suitable material and can have any desired configuration. For example, the device can be a container with a cover or open to the environment. Exemplary devices can be in the form of a dish, a centrifuge tube, a cell culture tube, or the like. The device can also be coupled to a fluidic interface.

The container and cover, if present, can be formed of any suitable material. Exemplary materials include, without limitation, glass, ceramic, polycarbonate, vinyl, polyvinyl chloride (PVC), polydimethylsiloxane (PDMS), acrylic, polypropylene, polyethylene, polyethyl sulfone (PES), and metal.

The cover can be formed of the same material as dish or the cover can be a membrane that facilitates gas exchange. Suitable gas permeable membranes have a thickness in the range of from about 10 to about 100 µm, preferably about 40 to about 60 µm. The membrane is placed over an opening in the side or top of the container. Membranes of this type are disclosed in U.S. Pat. No. 5,409,829 to Mussi et al., which is hereby incorporated by reference in its entirety.

To prevent excessive leakage of media and cells from the device, a gasket may be placed around the opening of the container and/or a solid plate placed under or alongside the opening and the assembly fastened together using any suitable a clasp mechanism. The substrate and nanoscale membrane are preferably inserted into the container such that any fluid communication between chambers occurs substantially, if not solely, through the nanoscale membrane(s).

Figure 3:
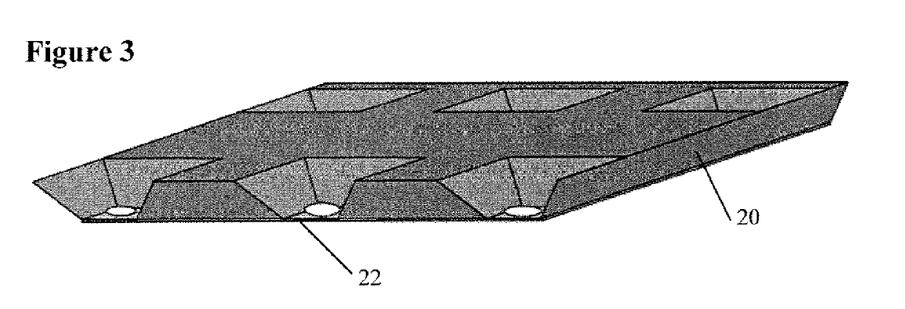

The nanoscale membrane(s) can be prepared in accordance with the procedures described in co-pending U.S. patent application Ser. No. 11/414,991 to Striemer et al., which is hereby incorporated by reference in its entirety. As described therein, procedures used for fabricating the nanoscale membranes can be used to control membrane properties, including its thickness, the range of pore sizes and mean pore size, and overall porosity. Moreover, procedures for manufacturing allow for the production of a plurality of membranes in a given substrate (see FIG. 3). For example, a single silicon wafer can be used to form more than a hundred (and potentially thousands of) membranes in a single substrate.

If the conditions employed during fabrication are substantially identical across the substrate, then the resulting membranes formed across the substrate should also be substantially the same (i.e., having substantially similar thickness, pore density, and pore dimensions). However, by modifying the conditions across the substrate, it becomes possible to achieve membranes that are different (i.e., having different thicknesses, pore densities, and/or pore dimensions). In the latter situation, for example, it may be possible to have several different types of membranes formed across a single substrate. Alternatively, different substrates can be joined together in a single device at or through a fluidic interface.

The nanoscale membrane can be formed of any number of materials that can afford suitable porosity for an intended use. Examples of suitable materials include, without limitation, semiconductor materials such as silicon, silicon alloys, p-doped silicon, and n-doped silicon; germanium; carbon; and metals such as gold, platinum, palladium, and aluminum. Of these, semiconductor materials are preferred, more preferably pure silicon or silicon that has been doped with one or more of B, Al, Ga, In, P, As, Sb, or Ge. The semiconductor material can be in either an amorphous form or a crystalline form, but preferably annealed into a nanocrystalline form. The examples provided herein demonstrate use of porous nanocrystalline silicon (pnc-Si) membranes, which are presently preferred.

The membranes formed of these materials can also be coated with any of a variety of coatings, including oxide coatings, electrically conductive coatings, dielectric coatings, etc. as described in pending U.S. patent application Ser. No. 11/414,991 to Striemer et al., which is hereby incorporated by reference in its entirety.

Depending on the intended use of the culture device that contains the membrane(s), it is possible to tailor the membrane properties to allow for cell to cell contact across a single membrane, to inhibit or in some instances preclude cell to cell contact across a membrane or multiple membranes, to allow diffusion of signaling molecules across the membrane, or to inhibit or in some instances preclude diffusion of signaling molecules across the membrane.

Thus, in certain embodiments, it is possible for the membrane(s) to have a thickness in the range of about 50 to about 100 nm, including membranes that are between about 90 and about 100 nm, between about 80 and about 90 nm, between about 70 and about 80 nm, between about 60 and about 70 nm, and between about 50 and about 60 nm. In other embodiments, it is possible for the membrane(s) to have a thickness in the range of about 10 to about 50 nm, including membranes that are between about 40 and about 50 nm, between about 30 and about 40 nm, between about 20 and about 30 nm, or between about 10 and about 20 nm. In still further embodiments, it is possible to for the membrane(s) to have a thickness that is less than about 10 nm, for example between about 2 nm and about 8 nm.

Consistent with the tunability of membrane thickness, it is possible to fabricate membranes characterized by a width to thickness aspect ratio that is more than $10^5$ to 1, more than $10^6$ to 1, and even approaching $10^7$ to 1.

Pore sizes of the membrane(s) can also be tailored. Using the procedures described in U.S. patent application Ser. No. 11/414,991 to Striemer et al., which is hereby incorporated by reference in its entirety, it is possible control the pore sizes during fabrication. Membranes having average pore sizes of less than about 50 nm in diameter can be prepared. More particularly, membranes can be prepared so as to tailor average pore sizes within the range of about 25 to about 50 nm, about 20 to about 25 nm, about 15 to about 20 nm, about 10 to about 15 nm, and about 2 to about 10 nm. Additional control over the pore size distribution can be achieved by slowly reducing the size of the as-formed pores by filling them in with another material. For example, the RF magnetron sputtering process for depositing amorphous silicon can be applied to the nanoporous membrane. Depositing approximately 1 nm of amorphous silicon could reduce the average pore diameter by as much as 2 nm. By carefully controlling this subsequent deposition, pore size distribution much smaller than those that can be formed directly, can be achieved.

The nanoscale membrane(s) can be tailored to have a pore density of between about $10^6$ and about $10^{12}$ per $cm^2$ of membrane, including between about $10^6$ and about $10^7$ per $cm^2$, between about $10^7$ and about $10^8$ per $cm^2$, between about $10^8$ and about $10^9$ per $cm^2$, between about $10^9$ and about $10^{10}$ per $cm^2$, between about $10^{10}$ and about $10^{11}$ per $cm^2$, and between about $10^{11}$ and about $10^{12}$ per $cm^2$.

The surface of the membrane(s) can be manufactured in a manner that affords substantially smooth (also known as locally smooth) surfaces containing few, if any, surface protrusions or irregularities. Alternatively, if it is desired for the surface not to be locally smooth, then the membrane can be fabricated in a manner that affords a textured surface (e.g., a relief pattern) that includes protrusions from one or both faces of the membrane at regular or random intervals.

After membrane fabrication, the membranes can be modified to include one or more reagents on its surface and/or inside its pores. Exemplary reagents that can be tethered to the surface(s) of one or both sides of the membrane(s) include, without limitation, cell surface receptors, antibodies, ligands, biological reagents, silanes having terminal groups, and combinations thereof.

A number of strategies are available for attaching one or more reagents to the surface of the porous membrane structure, i.e., modifying the membrane, depending upon the type of reagent which is ultimately to be attached thereto.

The available strategies for attaching the one or more reagents include, without limitation, covalently bonding a reagent to the surface of the membrane, ionically associating the reagent with the surface of the membrane, adsorbing the reagent onto the surface of the membrane, or the like. Such association can also include covalently or noncovalently attaching the reagent to another moiety (of a coupling agent), which in turn is covalently or non-covalently attached to the surface of the membrane.

Basically, an oxidized and hydrolyzed surface of the membrane is first functionalized (i.e., primed) with a coupling agent that is attached to the surface thereof. This is achieved by providing a coupling agent precursor and then covalently or non-covalently binding the coupling agent precursor to the surface of the membrane. Once the membrane surface has been primed, the reagent is exposed to the primed membrane under conditions effective to (i) covalently or non-covalently bind to the coupling agent or (ii) displace the coupling agent such that the probe covalently or non-covalently binds directly to the membrane surface. The binding of the reagent to the membrane is carried out under conditions that are effective to allow one or more target-binding groups thereon to remain available for binding to a target molecule. Many of these materials and coupling agents are described in U.S. patent application Ser. No. 10/082,634 to Chan et al., and U.S. patent application Ser. No. 10/282,274 to Miller et al., each of which is hereby incorporated by reference in its entirety.

Suitable coupling agent precursors include, without limitation, silanes functionalized with an epoxide group, a thiol, or an alkenyl; and halide containing compounds.

Silanes include a first moiety which binds to the surface of the membrane and a second moiety which binds to the reagent. Preferred silanes include, without limitation, 3-glycidoxypropyltrialkoxysilanes with C1-6 alkoxy groups, trialkoxy(oxiranylalkyl)silanes with C2-12 alkyl groups and C1-6 alkoxy groups, 2-(1,2-epoxycyclohexyl)ethyltrialkoxysilane with C1-6 alkoxy groups, 3-butenyl trialkoxysilanes with C1-6 alkoxy groups, alkenyltrialkoxysilanes with C2-12 alkenyl groups and C1-6 alkoxy groups, tris[(1-methylethenyl)oxy]3-oxiranylalkyl silanes with C2-12 alkyl groups, [5-(3,3-dimethyloxiranyl)-3-methyl-2-pentenyl]trialkoxysilane with C1-6 alkoxy groups, (2,3-oxiranediyldi-2,1-ethanediyl) bis-triethoxysilane, trialkoxy[2-(3-methyloxiranyl)alkyl]silane with C1-6 alkoxy groups and C2-12 alkyl groups, trimethoxy[2-[3-(17,17,17-trifluoroheptadecyl)oxiranyl]ethyl] silane, tributoxy[3-[3-(chloromethyl)oxiranyl]-2-methylpropyl]silane, and combinations thereof. Silanes can be coupled to the semiconductor structure according to methods which are well known to those of skill in the art.

Halides can also be coupled to the membrane, the conditions for which are well known to those of skill in the art.

Thereafter, the one or more reagents are bound to the membrane according to the type of functionality provided by the coupling agent. Typically, reagents are attached to the coupling agent or displace the coupling agent for attachment to the membrane in aqueous conditions or aqueous/alcohol conditions.

Epoxide functional groups can be opened to allow binding of amino groups, the conditions for which are well known to those of skill in the art. Epoxide functional groups can also be opened to allow binding of thiol groups or alcohols, the conditions for which are well known to those of skill in the art.

Alkenyl functional groups can be reacted to allow binding of alkenyl groups, the conditions for which are well known to those of skill in the art.

Where a halide coupling agent is employed, the halide coupling agent is typically displaced upon exposing the primed membrane to one or more reagents which contain alcohol groups as the membrane-binding groups. The conditions for halide coupling are well known to those of skill in the art.

Where the one or more reagents contain two or more target-binding groups, it is possible that the target-binding groups may also interact and bind to the primed surface of the membrane. To preclude this from occurring, the primed porous membrane can also be exposed to a blocking agent. The blocking agent essentially minimizes the number of sites where the one or more reagents can attach to the surface of the membrane. Exposure to the blocking agent can be carried out prior to exposing the primed surface of the membrane to the probes or simultaneous therewith, although simultaneous exposure is generally preferred. The blocking agents can be structurally similar to the reagents except that they lack a target-binding group or the blocking agents can simply be end-capping agents. By way of example, an amino acid alkyl ester (e.g., glycine methyl ester, glycine ethyl ester, 3-alanine methyl ester, etc.) blocking agent can be introduced to an epoxide-functionalized membrane surface for attaching a reagent to the coupling agent, except with the amino group of glycine opening the epoxide ring and covalently binding to the coupling agent.

The culture device of the present invention can have virtually any desired configuration. In its simplest form, the culture device includes a single lower chamber and a single upper chamber, with one or more nanoscale membranes positioned between the lower and upper chambers. Devices of this type typically contain a dish, tube, or other vessel, and a substrate possessing multiple membranes positioned in the dish, tube, or vessel to divide it into upper and lower chambers, and a simple cover that sits over the dish or closes the open mouth of the tube or vessel.

Referring now to the figures, preferred embodiments and constructions for the culture device will be described.

Figure 1A:
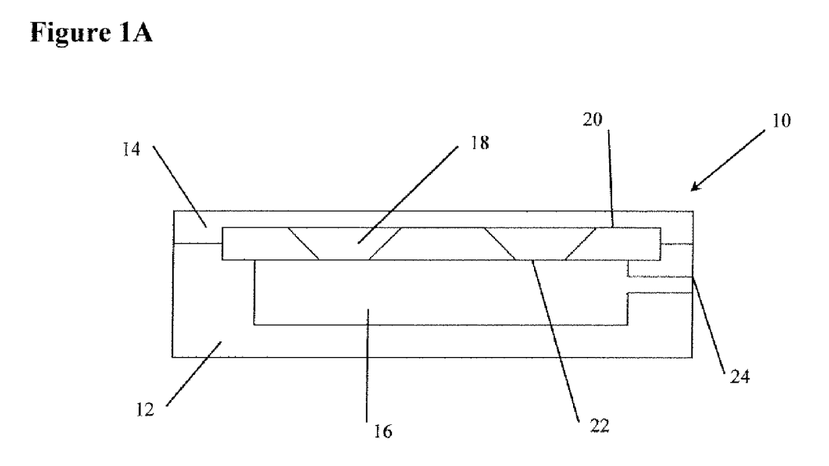
FIGS. 1A-B illustrate basic constructions of cell culture devices according to two embodiments of the present invention.

In FIG. 1A, the culture device 10 includes a container 12, a cover 14, and a substrate 20 that possesses multiple membranes 22 and is positioned over the container 12 to define a common lower chamber 16. A plurality of upper chambers or wells 18 are defined, at least in part, by the substrate itself and possibly the cover 14 (depending on whether the cover sits flush against the upper surface of the substrate). The container 12 can optionally include a port 24 that can be used to introduce and/or remove culture medium from lower chamber 16 (i.e., inlet and outlet are present in the single port). A valve can be provided to open and close the port as desired. Alternatively, separate inlet and outlet ports can be provided.

In this embodiment, culture medium can be provided in both the lower and upper chambers 16, 18 to allow for the growth of a first cell type in one of the chambers and a second cell type in the other of the chambers. The cell types in each of the upper chambers 18 can be the same or different across the device.

Figure 1B:
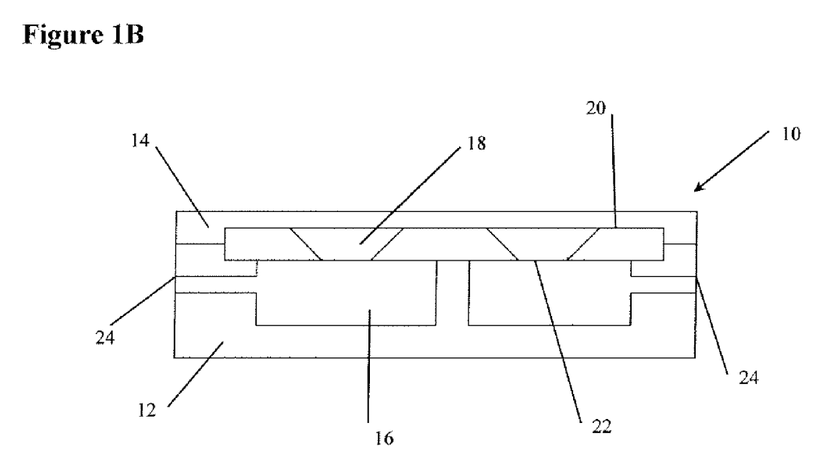

In FIG. 1B, the culture device 10 includes a container 12, a cover 14, and a substrate 20 that possesses multiple membranes 22 and is positioned over the container 12. The container includes a plurality of walls that divide the container into a plurality of distinct lower chambers 16. (Each lower chamber can optionally include a port 24 that can be used to introduce and/or remove culture medium. A valve can be provided to open and close each port as desired.) A plurality of upper chambers or wells 18 are defined, at least in part, by the substrate itself. The substrate and container are positioned relative to one another such that each upper chamber 18 corresponds to only a single lower chamber 16, with a single membrane 22 separating the upper and lower chambers.

In this embodiment, culture medium can be provided in both the lower and upper chambers 16, 18 to allow for the growth of a first cell type in one of the chambers and a second cell type in the other of the chambers. The cell types in each of the upper and lower chambers 16, 18 can be the same or different across the device. For example, each upper chamber 18 can possess a first cell type and each lower chamber can possess a second cell type, and different media can be used in the various pairs of chambers. This allows studying the effects of different environmental conditions on the same pairs of cell types. Alternatively, different pairs of cell types can be used in the lower and upper chambers, with the same or different culture medium, to study the different cell to cell influences with various environmental conditions.

Alternative constructions can also be used to afford more complex co-culturing capability (i.e., preventing direct cell-to-cell contact or using three or more cell types).

Figure 2A:
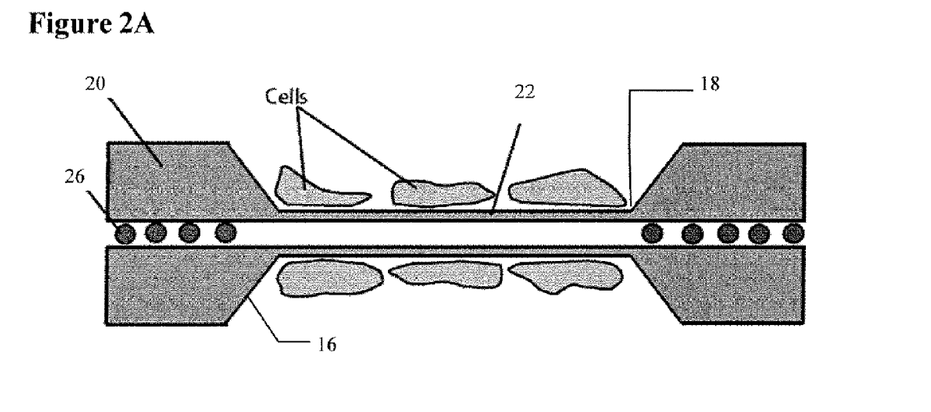
FIGS. 2A-C illustrate several alternative embodiments of cell culture devices. For simplicity, the entire device is not shown; instead, only the relationship between multiple membranes is illustrated.

Referring to FIG. 2A, a pair of substrates 20 can be used together to separate upper and lower chambers. The two substrates are positioned with their etched sides facing away from one another, and spacers 26 between them. This essentially creates a barrier zone between the upper chamber 18 and lower chamber 16 that is too large for the cells to communicate via cell to cell contact, but still allows cells to communicate via signaling molecules that can diffuse between the two chambers. The spacers 26 can simply separate the two substrates, or alternatively the spacers can form a fluid-tight seal.

The aligned membranes 22 that separate the lower and upper chambers 16, 18 can be substantially the same or different.

In this embodiment, culture medium can be provided in both the lower and upper chambers 16, 18 to allow for the growth of a first cell type in one of the chambers and a second cell type in the other of the chambers. The cell types in each of the upper and lower chambers 16, 18 can be the same or different across the device in the manner described above.

Figure 2B:
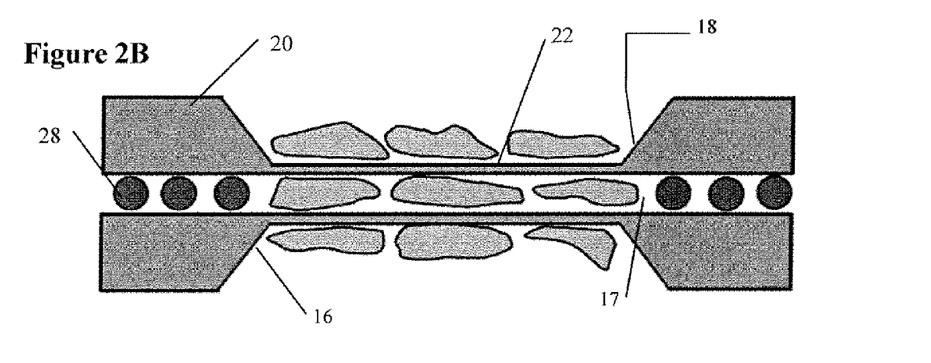

Referring to FIG. 2B, a pair of substrates 20 can be used together to separate upper and lower chambers. The two substrates are positioned with their etched sides facing away from one another, and spacers 28 between them. The spacers 28 are larger, for example, than spacers 26 in the embodiment of FIG. 2A, so as to form an intermediate (third) growth chamber 17. The spacers 28 can simply separate the two substrates such that the intermediate growth chamber 17 is in communication with all of the lower and upper chambers 16, 18, or alternatively the spacers 28 can form a fluid-tight seal around the membranes of the upper and lower substrates 20 so as to form multiple intermediate chambers 17. In the latter arrangement, each intermediate chamber 17 would correspond with only one lower chamber 16 and only one upper chamber 18.

The aligned membranes 22 that separate the lower, intermediate, and upper chambers 16, 17, 18 can be substantially the same or different.

In this embodiment, culture medium can be provided in the lower, intermediate, and upper chambers 16, 17, 18 to allow for the growth of a first cell type in one of the chambers, a second cell type in another chamber, and a third cell type in the other chamber. The cell types in each of the lower, intermediate, and upper chambers 16, 17, 18 can be the same or different across the device in the manner described above.

Figure 2C:
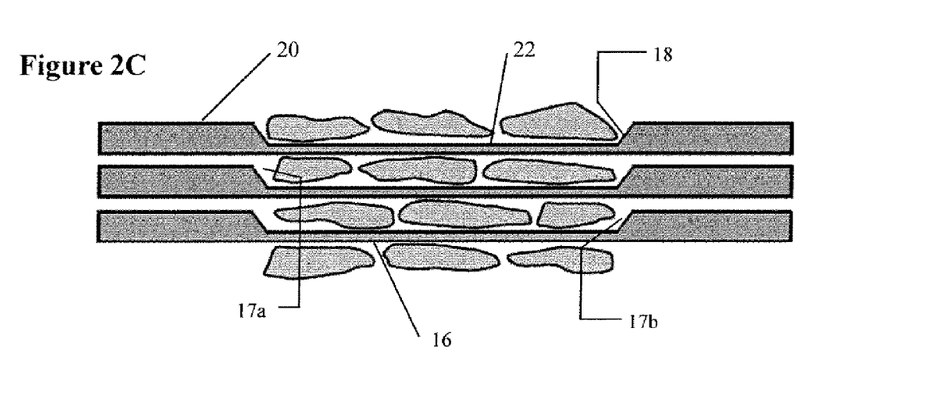

Referring to FIG. 2C, three (or more) substrates 20 can be stacked with their etched sides facing in the same direction to create multiple chambers. In this arrangement, each of the chambers defined by a single substrate is in communication with the chambers immediately above or below (as defined by the stacked substrates 20 and/or container 12. As shown, three substrates 20 are stacked to form lower and upper chambers 16, 18, as well as two intermediate chambers 17a and 17b. Any number of substrates 20 can be stacked between a container 12 and cover 14, depending on the height allowance for the container 12.

The aligned membranes 22 that separate the lower, intermediate, and upper chambers 16, 17a, 17b, 18 can be substantially the same or different.

In this embodiment, culture medium can be provided in the lower, intermediate, and upper chambers 16, 17a, 17b, 18 to allow for the growth of a first cell type in one of the chambers, a second cell type in another chamber, a third cell type in yet another chamber, and a fourth chamber in the other chamber. The cell types in each of the lower, intermediate, and upper chambers 16, 17a, 17b, 18 can be the same or different across the device in the manner described above. This allows the formation of complex in vitro tissue structures.

As described above, the membrane properties can be tightly controlled to permit certain cell-to-cell interactions while precluding or inhibiting others. Examples of such control are shown in FIGS. 4A-C.

Figure 4A:
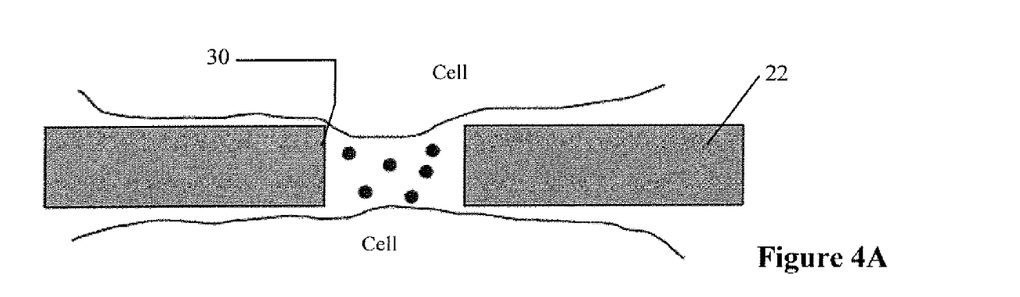
FIGS. 4A-C illustrate the effects of varying thickness and pore sizes.

FIG. 4A illustrates a membrane 22 that is sized (i.e., less than about 20 nm thick) to allow diffusion of signaling molecules but is characterized by pore 30 dimensions (i.e., less than about 5 nm) that preclude or at least discourage direct cell-to-cell contact.

Figure 4B:
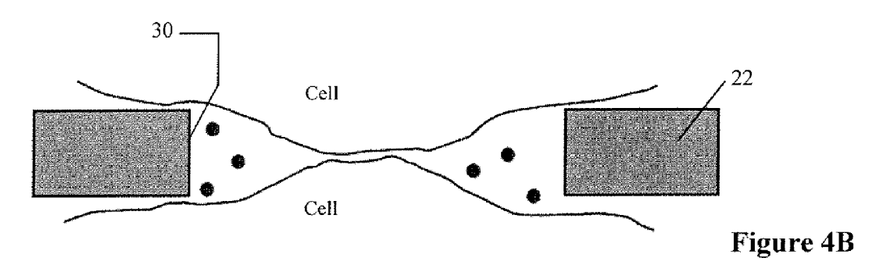

FIG. 4B illustrates a membrane 22 that is sized (i.e., less than about 30 nm thick) to allow diffusion of signaling molecules but is characterized by pore 30 dimensions (i.e., greater than about 30 nm) that encourage direct cell-to-cell contact.

Figure 4C:
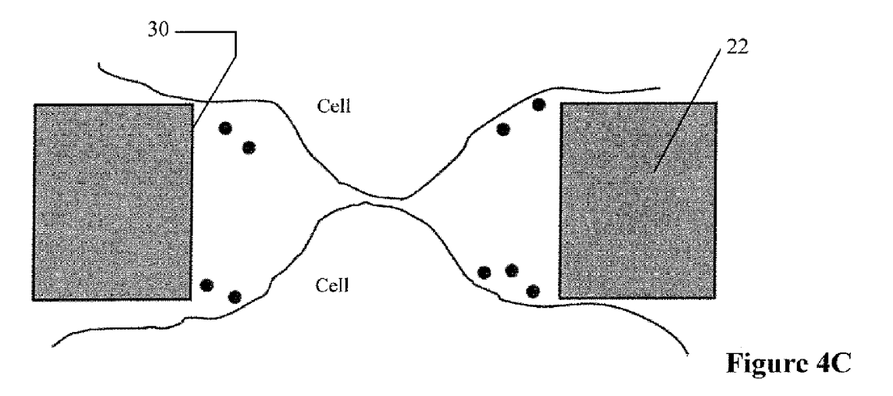

FIG. 4C illustrates a membrane 22 that is sized (i.e., about 100 nm thick or greater) to discourage diffusion of signaling molecules but is characterized by pore 30 dimensions (i.e., greater than about 50 nm) that encourage direct cell-to-cell contact.

In addition to using the membrane thickness, pore size, and presence of tethered molecules to regulate the growth of cells in the respective chambers, other modifications of membrane properties, the use of a scaffold in one or more growth chambers, and the appropriate selection of culture media can also regulate cell growth and/or differentiation.

The properties of the membranes can be modified by introducing a charge across the membranes. Introducing a charge to the membrane can be performed by contacting the membrane with an electrode in the manner described in co-pending U.S. patent application Ser. No. 11/414,991 to Striemer et al., which is hereby incorporated by reference in its entirety. For example, by positively charging the membrane it is possible to preclude passage of positively charged molecular species across the membrane while allowing passage of negatively charged species. Likewise, by negatively charging the membrane it is possible to preclude passage of negatively charged molecular species across the membrane while allowing passage of positively charged species. In addition, the introduction of a charge to the membrane will typically promote cell growth.

Any number of three-dimensional scaffolds can be used, particularly when it is desired to culture two or more cell types together in a single chamber. Preferably, the three-dimensional scaffold mimics the natural extracellular matrix and provided ample surface area to allow cell to cell interaction at a tissue-like cell density that occurs in native tissues. Cell culture devices of this type have been described in detail in U.S. patent application Ser. No. 09/715,852 to Wu et al., filed Nov. 17, 2000, and Ser. No. 09/796,830 to Wu et al., filed Mar. 1, 2001, each of which is hereby incorporated by reference in its entirety.

The scaffolding may consist of tangled fibers, porous particles, or a sponge or sponge-like material. Suitable scaffolding substrates may be prepared using a wide variety of materials including, without limitation, natural polymers such as polysaccharides and fibrous proteins; synthetic polymers such as polyamides (nylon), polyesters, polyurethanes; semi-synthetic materials; minerals including ceramics and metals; coral; gelatin; polyacrylamide; cotton; glass fiber; carrageenans; and dextrans. Exemplary tangled fibers include, without limitation, glass wool, steel wool, and wire or fibrous mesh. Examples of porous particles include, without limitation, beads (glass, plastic, or the like), cellulose, agar, hydroxyapatite, treated or untreated bone, collagen, and gels such as Sephacryl, Sephadex, Sepharose, agarose or polyacrylamide. "Treated" bone may be subjected to different chemicals such as, acid or alkali solutions. Such treatment alters the porosity of bone. If desired, the substrate may be coated with an extracellular matrix or matrices, such as, collagen, matrigel, fibronectin, heparin sulfate, hyaluronic and chondroitin sulfate, laminin, hemonectin, or proteoglycans.

The scaffolding essentially has a porous structure, with the pore size being determined by the cell types intended to occupy the device. One of skill in the art can determine the appropriate pore size and obtain suitable scaffolding materials that can achieve the desired pore size. Generally, a pore size in the range of from about 15 microns to about 1000 microns can be used. Preferably, a pore size in the range of from about 100 microns to about 300 microns is used.

Any suitable culture media can be employed in the culture device of the present invention. For instance, the culture media can be placed in the lower, intermediate, and at least a portion of the upper chambers. The culture medium preferably covers any scaffold present in the chamber(s). Suitable culture media need to support the growth and differentiation of cells of various tissues and (optionally) any accessory cells included therein. The culture media can be supplemented with any growth factors, metabolites, etc.

Exemplary culture media include, without limitation, (i) classical media such as Fisher's medium (Gibco), Basal Media Eagle (BME), Dulbecco's Modified Eagle Media (D-MEM), Iscoves's Modified Dulbecco's Media, Minimum Essential Media (MEM), McCoy's 5A Media, and RPMI Media, optionally supplemented with vitamin and amino acid solutions, serum, and/or antibiotics; (ii) specialized media such as MyeloCuht™ (Stem Cell Technologies) and Opti-Cell™ (ICN Biomedicals) or serum free media such as Stem-Span SFEM™ (StemCell Technologies), StemPro 34 SFM (Life Technologies), Marrow-Gro (Quality Biological Inc.), and EBM2 (Bio Whittaker) for endothelial cells. A preferred media for bone marrow includes McCoy's 5A medium (Gibco) used at about 70% v/v, supplemented with approximately $1 \times 10^{-6}$ M hydrocortisone, approximately 50 µg/ml penicillin, approximately 50 mg/ml streptomycin, approximately 0.2 mM L-glutamine, approximately 0.45% sodium bicarbonate, approximately 1× MEM sodium pyruvate, approximately 1× MEM vitamin solution, approximately 0.4× MEM amino acid solution, approximately 12.5% (v/v) heat inactivated horse serum and approximately 12.5% heat inactivated FBS, or autologous serum.

Because the substrate and membranes of the present invention can be sterilized, e.g., by autoclaving, it is not critical for the membranes to be manufactured and packaged under sterile conditions. Nevertheless, it may be desirable to do so, in which case the substrate and membranes can be sterilized and then sealed within the confines of a sterile package. Alternatively, the entire culture device can be sterilized and then sealed within the confines of a sterile package.

The culture device of the present invention can also be present in the form of a kit. In certain embodiments, the kits can include a single substrate having at least one but preferably a plurality of membranes, and a plurality of containers for culturing cells. This embodiment allows the user to sterilize the substrate and membrane(s) after each use, and supply a new container each time the culture device is to be used. In another embodiment, one or more culture devices are provided but replacement containers are not included.

Regardless of the embodiment, the kit may optionally include one or more of the following additional components: (i) a cell culture medium, such as the types described above, (ii) one or more cell lines, and (iii) instructions for the co-culturing of one or more cells.

The present invention also relates to a method of co-culturing two or more populations of cells. Using a culture device of the present invention, a first population of cells can be grown in culture medium present in the first chamber and a second population of cells can be grown in culture medium present in the second chamber (i.e., on opposite sides of the nanoscale membrane that separates the first and second chambers). In this manner, the cells are physically separated yet are able to contact and/or communicate with each other, as desired, through the plurality of pores in the membrane. As noted above, the membrane properties can be selected, as desired, to allow or to inhibit/preclude direct cell-to-cell contact or cell signaling. Where multiple chambers are provided, three or more cell types can be grown in a similar manner.

When it is only desired to maintain a single cell population in isolation, multiple cell types can be cultured in one chamber, i.e., on one side of the membrane(s), and the single cell population to remain isolated can be cultured in the other chamber on the opposite side of the membrane. This may be desirable when the multiple cell types cultured together are used to alter or stimulate growth or differentiation of cells on the other side of the membrane, but are not themselves intended to be recovered in pure form.

The culture devices of the present invention can also be incorporated into micro-fluidic devices such that a constant or periodic (but frequent) flow of fresh, oxygenated culture media can be introduced into the chambers of the device. The device can also include perfusion chambers to allow exchange of medium and, possibly, recycling of medium from one chamber to a different chamber. In this embodiment, it is also possible for different culture media to be introduced into the different chambers of the device. Thus, the culture media can differ in one or more properties such as pH, proteins, ions, or other supplements. By constantly or frequently introducing fresh culture media, it is possible to maintain a gradient across the membrane.

Any combination of harvested (and optionally purified) primary cell types or in vitro cell lines can be cultured in the culture devices of the present invention. The cell types can be derived from an animal, a bacteria, a fungus, yeast, algae, and/or a plant. Animal cells, particularly mammalian cells, are preferred.

The types of cells that can be cultured are not particularly limited, and the devices of the present invention can be used for, for example, various cultured animal cells. More specifically, the methods can be applied for culturing primary cell isolates or cells of established cell lines derived from various organs such as liver, kidney, lung, stomach, spleen, nerve, muscle, skin, and bones as well as various cancer cells. Examples include, without limitation, cells derived from embryonic epiderm, mesoderm, or endoderm; stem cells such as embryonic stem cells, somatic stem cells, hematopoietic stem cells, mesenchymal stem cells, and neural stem cells; immunological cells such as T cells, T regs, dendritic cells, antigen presenting cells, etc.; epithelial cells including keratinocytes and melanocytes; vascular tissue cells including vascular endothelial cells and vascular smooth muscle cells; neural cells including neurons and glial cells such as astrocytes, ependymal, and sub-ependymal cells; hair metrocytes; bone cells including osteoblasts and osteoclasts; chondrocytes; hepatocytes; stellate cell; amnion-derived cells and fetal cells including fetal liver-derived cells, fetal kidney-derived cells, and fetal lung-derived cells; as well as cells of established cell lines including HeLa cells, FL cells, KB cells, HepG2 cells, WI-88 cells, MA104 cells, BSC-1 cells, Vero cells, CV-1 cells, BHK-21 cells, L cells, CHL cells, BAE cells, BRL cells, PAE cells, and the like. The genes of any of these cells may be artificially manipulated prior to culturing.

It is also desirable to culture different combinations of cells including, without limitation: astrocytes and endothelial cells, optionally with glial cells; astrocytes and neurons, optionally with glial cells; natural killer T-cells and dendritic cells; stem cells with helper cells or neurons; and endothelial cells and vascular smooth muscle cells; T cells and T regulator cells (optionally with antigen presenting cells); epiderm- and mesoderm-derived cells; and embryonic germ cell co-cultures including cells derived from two or more of epiderm-, mesoderm-, and endoderm-derived cells.

Once the co-culturing of cells has achieved its purpose, one or more types of cultured cells can be collected using any suitable collection techniques. For example, non-adherent cells can be collected by perfusing the chamber and any three-dimensional matrix with phosphate buffered saline (PBS). This non-adherent fraction can be counted and analyzed separately from the adherent fraction, or the two fractions can be pooled as desired. Adherent cells can be harvested by incubating the device for 7 minutes at 37° C. with 0.05% trypsin or by incubating the device with CDS (Sigma). The removed adherent cells can be collected and rinsed with medium. These techniques reproducibly result in high viable cell recovery. These techniques may be particularly desirable when the collected cells are needed for therapeutic administration, or for further study.

By virtue of co-culturing different cell types in the device of the present invention, it is possible to create in vitro models of various tissues. In one embodiment, the in vitro tissue model includes two cell types segregated on opposite sides of the membrane, and the two cell types are capable of cell-to-cell contact across the membrane and/or small molecule-mediated cell-to-cell communication. In another embodiment, the in vitro tissue model includes at least three cell types segregated on opposite sides of at least two membranes, where the segregated cell types are capable of cell-to-cell contact across the membranes and/or small molecule-mediated cell-to-cell communication.

Using the culture device of the present invention, it is possible to simulate a number of tissues. Exemplary tissues include, without limitation: (i) vascular tissue by co-culturing endothelial and smooth muscle cells; (ii) tumor cell microenvironments; (iii) the blood brain barrier by co-culturing cerebral endothelial cells, astrocytes, and pericytes; and (iv) the lining of the gut.

By way of example with the in vitro blood brain barrier, this tissue mimic can be used to assess the ability of a drug to cross the blood brain barrier. Basically, a drug is introduced into one chamber of the device and then an assessment is made with respect to the concentration of drug that has crossed the blood brain barrier mimic into the other chamber. This can be measured by using labeled drugs, including radiolabeled drugs or fluorescently tagged drugs, etc. This particular embodiment is useful for assessing the therapeutic potential of a particular drug with respect to treatments of the brain.

In yet another example, an in vitro gut lining can be prepared in accordance with the present invention and then used to assay the ability of the drug to cross the gut lining. Basically, a drug is introduced into one chamber of the device and then an assessment is made with respect to the concentration of drug that has crossed the gut lining mimic into the other chamber. This can be measured by using labeled drugs as described above. This particular embodiment is useful for assessing whether oral delivery of a particular drug will likely be effective. Dosage schedules during animal trials can be set based upon the in vitro data generated using the in vitro gut lining of the present invention.

In another embodiment of the in vitro tissue model, the membrane can be used in the absence of separate chambers per se. In this embodiment, the membrane can be released from the substrate and then used to fabricate a three dimensional structure. Different cell types can be seeded onto the interior of the structure versus the exterior of the structure.

Figure 5:
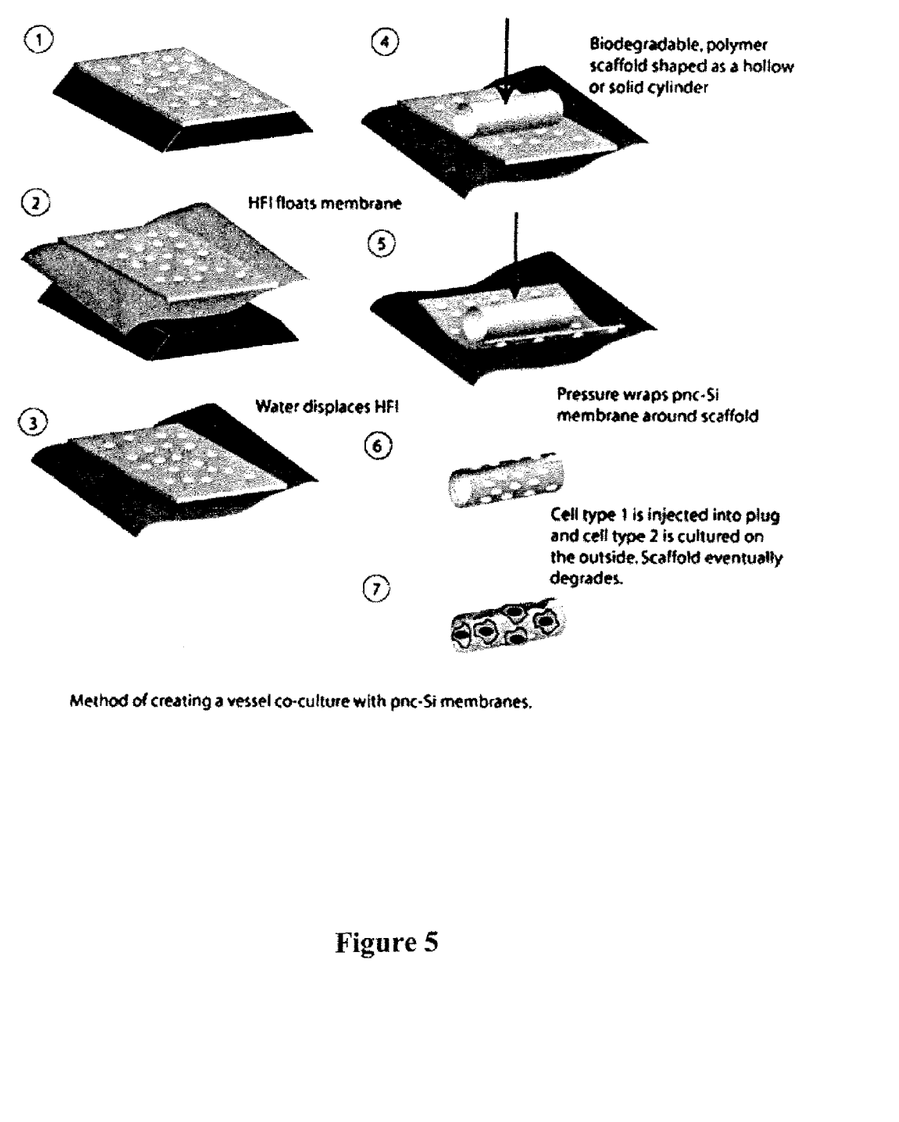
FIG. 5 illustrates a process for forming a three-dimensional in vitro tissue model for replicating vascular structure and/or vascular grafts. A similar process can be used to prepare nerve guides.

A process for forming an in vitro vascular tissue model is illustrated in FIG. 5. A substrate is provided that possess at least one nanoscale membrane. The membrane can be released from the substrate using, e.g., a buffered oxide etchant for anywhere from about 5 to about 30 minutes. Water can be used to halt the etching process. Thereafter the released membrane is wrapped around a three-dimensional structure (e.g., a cylinder) to form a three-dimensional membrane structure that can be seeded with one or more cell types externally and internally of the structure.

The three-dimensional structure can be partly or wholly composed of suitable biopolymer material can also be applied to the internal surface of the membrane. Suitable biopolymer films are well known in the art and include resorbable or biodegradable polymers. Exemplary biodegradable polymers include, without limitation, poly(ethylene co-vinyl acetate), poly(lactide co-glycolide), poly(caprolactone) poly(lactide), polyglycolide, polyanhydride, polyorthoester, polyphosphazene, proteinaceous polymer, polyester, silicone, or combinations thereof. Depending on how long the structure resides in the culture medium, the biopolymer may degrade over time.

According to one embodiment, endothelial cells are seeded on the internal surface of the membrane and smooth muscle cells are seeded on the external surface of the membrane. The seeded structure, when placed in a cell culture medium, will allow for growth and development of the seeded cells, thereby forming the in vitro vascular tissue model. Use of this in vitro tissue as a vascular graft is also contemplated.

According to another embodiment, nerve cells are seeded on the internal surface of the membrane and astrocytes are seeded on the external surface of the membrane. The seeded structure, when placed in a cell culture medium, will allow for growth and development of the seeded cells, thereby forming the in vitro nerve tissue model.

The cell culture devices of the present invention can also be used to monitor the signaling behavior of cells. This can be accomplished by monitoring the diffusion of secreted signaling molecules, even those present in low abundance. Any signaling molecule that possess a natural or synthetic receptor can be studied in a device of the present invention.

Cell signaling molecules worthy of study include those that fall into the class of short distance signaling molecules. Exemplary short distance signaling molecules include, without limitation, members of the Wnt family, members of the hedgehog family, notch family members, interferon family members, molecules that recognize toll-like receptors such as PAMPs, lymphokines, chemokines, cytokines, hormones, interleukins, molecules recognizing receptors of the Immunoglobulin super family (e.g., IL-1), molecules recognizing receptor tyrosine kinase receptors (e.g., FGF, HGF, etc.), molecules recognizing receptor serine/threonine kinase receptors (e.g., TGF-$\beta$, BMP, BMP inhibitor, etc.), and molecules recognizing seven transmembrane helix receptors (e.g., fMLP, IL-8, etc.).

The monitoring of low abundance molecular species can be carried out by providing a culture device as described herein with cell cultured in one of the chambers, and then detecting the presence of the low abundance molecular species in another chamber of the culture device. Detecting the presence of the low abundance species can be carried out with or without fixing the cells in the chamber, by staining and/or labeling the low abundance molecular species, or by using a labeled detection reagent.

Detection of the low abundance molecular species can be achieved in any number of ways. When using genetically modified cells to produce the molecular species to be detected, the molecular species is preferably expressed as a fusion protein that includes a fluorescent protein or polypeptide that can participate in fluorescent resonance energy transfer or FRET. A receptor that is specific for the fusion protein to be detected also includes a fluorophore capable of participating in FRET with the fluorescent protein or polypeptide of the fusion protein. Alternatively, detection can be achieved using a sandwich ELISA format using antibodies specific for the molecular species to be detected. For example, the chamber in which detection occurs can also include one or more receptors specific for the molecular species to be detected, and these receptor-bound species can be detected using labeled antibodies, antibody fragments, or antibody mimics.

Figure 6:
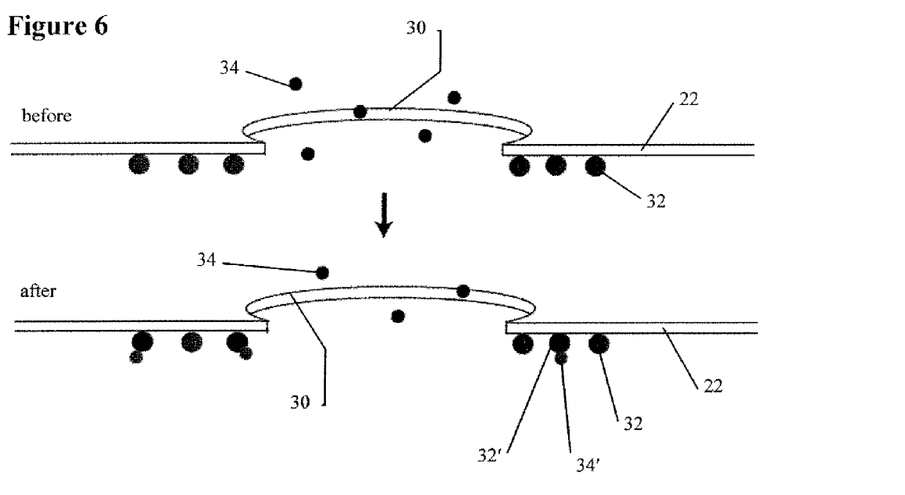

According to one embodiment, shown in FIG. 6, a plurality of receptor molecules 32 are tethered to at least one side of the membrane 22. The low abundance molecular species 34 will diffuse through the pore 30 where they can bind to the receptor molecules 32. Binding of the species 34 to the receptor 32 can be indicated by a change in fluorescent emissions from one or both of the species 34 and receptor 32. In this embodiment, the species and receptor include fluorescent proteins or polypeptides capable of participating in FRET. Consequently, binding results in a detectable change in the fluorescent signal.

A still further aspect of the present invention relates to the visualization of cells that are cultured in the devices of the present invention. Because the membranes of the present invention are penetrable by light (thickness $<<\lambda$), cells on either side of the membrane can be observed using traditional light microscopy, Darkfield microscopy, Brightfield microscopy, differential interference contrast microscopy, phase contrast microscopy, polarized light microscopy, confocal microscopy, near-field scanning optical microscopy, fluorescence microscopy, scanning electron microscopy, or transmission electron microscopy. Moreover, because certain membranes of the present invention are porous to some dyes, cells on both sides of the membrane can be stained or otherwise labeled as desired prior to observation. The cells can optionally be fixed prior to staining as is well known in the art.

EXAMPLES

Each of the following examples are provided to illustrate embodiments of the present invention but are by no means intended to limit its scope.

Example 1

Formation of Culture Device

A silicon substrate containing a plurality of porous nanoscale membranes was prepared in accordance with the procedures described in co-pending U.S. patent application Ser. No. 11/414,991 to Striemer et al., which is hereby incorporated by reference in its entirety. The membranes were formed under identical conditions and, therefore, are believed to be substantially similar in their properties. The membranes have an average thickness of about 15 nm, a mean pore size of about 25 nm.

The silicon substrate containing the membranes will be used to prepare a culture device that inserts into standard format "6 well" culture dishes available from a variety of manufacturers including Coming and Falcon. A 2 cm diameter silicon chip containing ~80% active membrane area will be supported by a plastic structure that fits into the well so as to suspend the membrane roughly 1 cm from the floor of the well. The plastic structure will seal the membrane so that fluid and molecules cannot traverse from the bottom to the top chambers defined by the membrane except through the membrane's pores. The design of this plastic insert will be similar to commercially available inserts that suspend filter membranes in cell culture vessels and centrifuge tubes, and are commercially available from such manufacturers as Pall, Millipore, and Corning.

Example 2

Porous Nanocrystalline Silicon Membranes Withstand Autoclaving

Because culture devices or at least the substrate containing the membranes will need to be sterilized prior to packaging (and use), the ability of a porous nanocrystalline silicon membrane to withstand autoclaving was assessed.

Figure 7A:
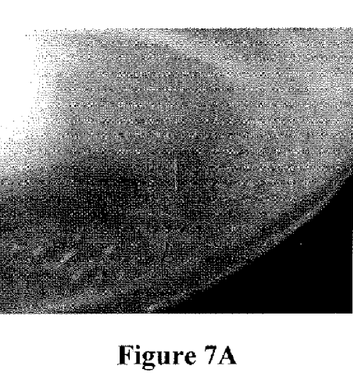
FIGS. 7A-B illustrate a silicon substrate that includes three porous nanocrystalline silicon (pnc-Si) membranes, one of which has been intentionally broken to facilitate examination of the other remaining pnc-Si membranes after autoclaving. The before (7A) and after (7B) images show no deleterious effect of autoclaving on the unbroken pnc-Si membranes.
Figure 7B:
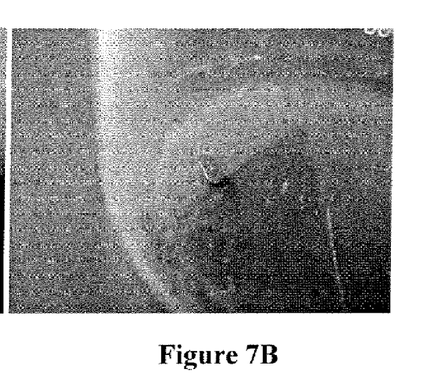

A three-well pnc-Si membrane sample was exposed to autoclaving conditions of 121° C. at 15 psi. Images of the membrane were obtained before and after autoclaving (FIGS. 7A-B). One of the three membranes was broken intentionally before autoclaving to create a clear difference between intact and broken membranes. The images show two membranes remain intact and after standard autoclaving procedures.

Example 3

Immortalized Fibroblasts Grown on pnc-Si Membranes

Immortalized fibroblasts were grown on non-oxidized pnc-Si membranes (removed from their substrate) and standard glass coverslips.

Membranes and cover slips were sterilized in methanol and allowed to dry before transferring them to a six-well dish. The membranes were anchored to the well surface using a dot of vacuum grease. Cells were split to low density (3 drops to each well) and incubated with 5% $CO_2$. At each time point, the cover slip and membrane to be stained were removed from the six well plates and placed in a transfer dish containing medium to move it to a fume hood. In the fume hood, the cells were fixed with 3.7% Formaldehyde in PBS for 15 minutes. After fixation, the membrane and cover slip were rinsed in distilled water and stained using actin stain solution. (Actin stain solution is 10% 10X PHEM buffer (6.9), 1% TX-100 Triton, 87% dd$H_2O$, and 2% secondary dilution of Phalloidin FITC. The secondary dilution is 10 Lf Phalloidin FITC in 80 μl DMSO. The membrane and cover slip were soaked in stain for 7 minutes while covered with a foam lid, to keep light from attacking the phalloidin. Once stained, they were washed again in distilled water and mounted on glass slides.

Figure 8A:
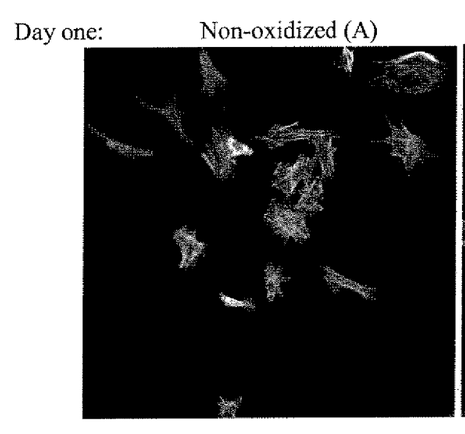
FIGS. 8A-F are images of fibroblasts grown on non-oxidized porous nanocrystalline silicon membranes (8A, 8C, 8C) and glass cover slips (8B, 8D, 8F). Cells were visualized by light microscopy.
Figure 8B:
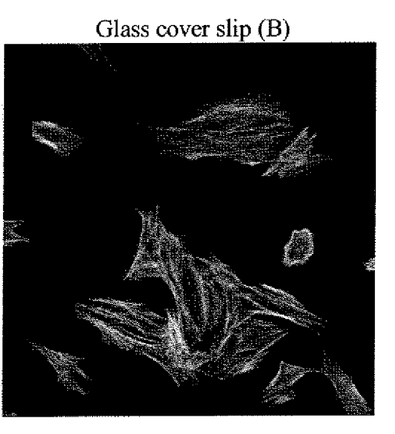
Figure 8C:
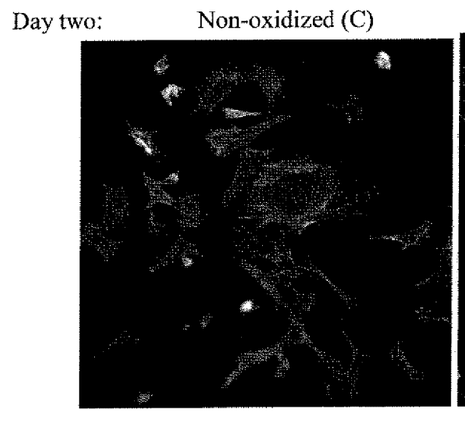
Figure 8D:
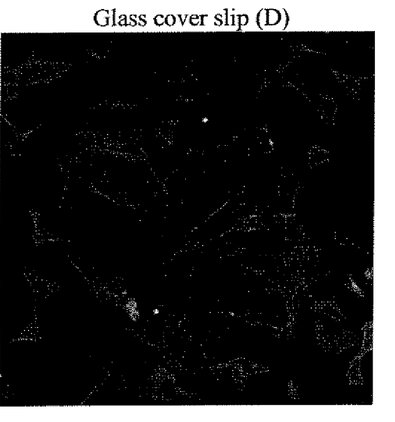
Figure 8E:
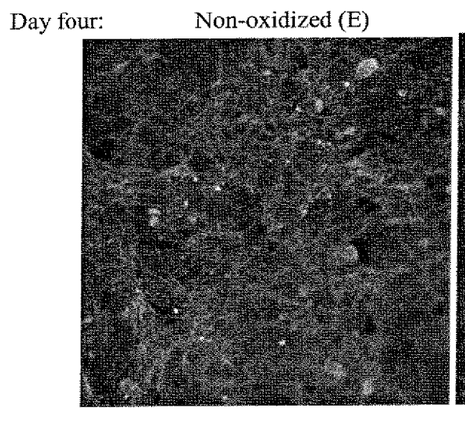
Figure 8F:
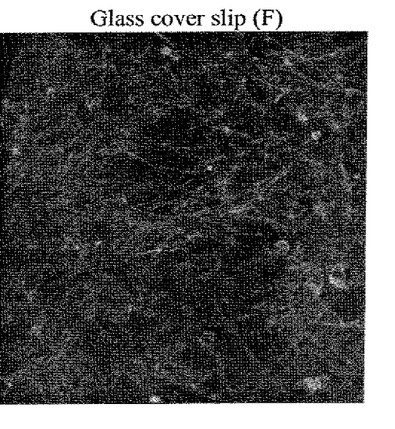

Imaging was done on a Zeiss Axiovert 200m microscope using fluorescent light. Photos were taken at three time points: day one, day two, and day four. FIGS. 8A, C, and E illustrate images of dye-stained fibroblasts growing on the non-oxidized pnc-Si membrane. The morphology of the cells demonstrates that they are well spread, and the population grew to confluence by day 4 (FIG. 8E). Growth to confluence was delayed slightly as compared to the fibroblasts grown on the cover slips (compare FIGS. 8B, D, and F).

Example 4

Co-Culturing of Astrocytes and Endothelial Cells

A culture device as described in Example 1 will be used to separate a lower compartment from an upper compartment. The compartments will both be filled with the serum-supplemented DMEM. Endothelial cells will first be adhered to the lower surface of the filter with the insert inverted in a larger culture vessel. This will allow cells to settle onto the backside of the membrane surface via gravity. Non-adhered cells will be washed off the backside after about 4 hours and the insert will be transferred to a well in a standard 6-well formatted culture dish and suspended so that the endothelial cells are facing the bottom of the well. Astrocytes will then be introduced into the upper compartment and will settle by gravity until the contact and adhere to the second membrane surface.

The cell types will be cultured until they have grown to confluence, with the culture medium being changed every 48 hours.

The resulting cultures will be exposed to drugs introduced into the lower chamber to assess the ability of the drugs to pass the in vitro blood-brain barrier.

Example 5

Co-Culturing of Mid-Brain Astrocytes and Human Embryonic Stem Cells

A culture device as described in Example 1 will be used to separate a lower compartment from an upper compartment. The compartments will both be filled with the DMEM-F12 supplemented with growth factor and 10% FBS. Mid-brain astrocytes will first be adhered to the lower surface of the filter with the insert inverted in a larger culture vessel. This will allow astrocytes to settle onto the backside of the membrane surface via gravity. Non-adhered cells will be washed off the backside after about 4 hours and the insert will be transferred to a well in a standard 6-well formatted culture dish and suspended so that astrocytes are facing the bottom of the well. The human embryonic stem cells will then be introduced into the upper compartment and will settle by gravity until the contact and adhere to the second membrane surface.

The cells will be cultured until they have grown to confluence, with the culture medium being changed every 24 hours.

The human embryonic stem cells will be inspected for evidence of a neuronal phenotype using stains for the proteins expressed in neuronal lineages: nesting, engrailed 1, etc.

Example 6

Co-Culturing of Natural Killer T-Cells and Dendritic Cells

A culture device as described in Example 1 will be used to separate a lower compartment from an upper compartment. The compartments will both be filled with the RPMI 1640 medium. The T-cells will first be adhered to the lower surface of the filter with the insert inverted in a larger culture vessel. This will allow T-cells to settle onto the backside of the membrane surface via gravity. Non-adhered cells will be washed off the backside after about 4 hours and the insert will be transferred to a well in a standard 6-well formatted culture dish and suspended so that T-cells are facing the bottom of the well.

Dendritic cells will be separately exposed to either bacterial or viral antigen including but not limited to proteins, polysaccharides, lipoproteins, or glycolipids for between 3 and 6 days. The primed dendritic cells will then be introduced into the upper compartment and will settle by gravity until they contact and adhere to the second membrane surface. The co-culture with T cells will be maintained for between 15 minutes and 9 days. The culture medium will be changed, if necessary, every 24 to 48 hours.

T cells will be harvested and tested for signs of activation due to co-culture with antigen presenting dendritic cells.

Although the invention has been described in detail for purposes of illustration, it is understood that such detail is solely for that purpose, and variations can be made therein by those skilled in the art without departing from the spirit and scope of the invention as defined in the claims that follow.

What is claimed:

1. A cell culture device comprising:
    first and second chambers separated by at least one nanoscale semiconductor membrane positioned between the first and second chambers, the at least one nanoscale membrane having an average thickness of less than about 100 nm, and having a plurality of pores extending between opposite sides thereof.

2. The device according to claim 1 further comprising cell culture medium in the first and second chambers, a first cell type in the first chamber, and a second cell type in the second chamber.

3. The device according to claim 1, wherein the device comprises a plurality of first chambers and one second chamber in communication with each of the plurality of first chambers through the at least one nanoscale membrane.

4. The device according to claim 3 further comprising cell culture medium in the plurality of first chambers and the one second chamber.

5. The device according to claim 4 further comprising a first cell type in each of the plurality of first chambers.

6. The device according to claim 5 further comprising a second cell type in the one second chamber.

7. The device according to claim 4 further comprising two or more different cell types separately residing in the plurality of first chambers.

8. The device according to claim 7 further comprising a further cell type in the one second chamber.

9. The device according to claim 1, wherein the device comprises a plurality of paired first and second chambers, with each second chamber in communication with only one first chamber through the at least one nanoscale membrane.

10. The device according to claim 9 further comprising cell culture medium in the plurality of paired first and second chambers, a first cell type in the first chambers, and a second cell type in the second chambers.

11. The device according to claim 10, wherein the first cells types are the same in each of the first chambers and the second cell types are the same in each of the second chambers.

12. The device according to claim 10, wherein the first cells types are different in each of the first chambers and the second cell types are the same or different in each of the second chambers.

13. The device according to claim 1 further comprising:
    an intermediate chamber positioned between the first and second chambers, the intermediate chamber being separated from each of the first and second chambers by one or more of the at least one nanoscale membranes.

14. The device according to claim 13 wherein the at least one nanoscale membrane separating the first chamber and the intermediate chamber is substantially the same as the at least one nanoscale membrane separating the second chamber and the intermediate chamber.

15. The device according to claim 13 wherein the at least one nanoscale membrane separating the first chamber and the intermediate chamber is different from the at least one nanoscale membrane separating the second chamber and the intermediate chamber.

16. The device according to claim 13 further comprising cell culture medium in the first, second, and intermediate chambers.

17. The device according to claim 16 further comprising a first cell type in the first chamber and a second cell type in the second chamber.

18. The device according to claim 17 further comprising a third cell type in the intermediate chamber.

19. The device according to claim 1, wherein at least one of the chambers comprises a three-dimensional scaffold.

20. The device according to claim 1, wherein the at least one nanoscale membrane precludes cell-to-cell contact between cells grown on opposite sides thereof.

21. The device according to claim 1, wherein the at least one nanoscale membrane promotes cell-to-cell contact between cells grown on opposite sides thereof.

22. The device according to claim 1, wherein the at least one nanoscale membrane comprises a plurality of spaced nanoscale membranes positioned between the first and second chambers.

23. The device according to claim 22, wherein each of the plurality of nanoscale membranes is characterized by a substantially similar thickness, pore density, and pore dimensions.

24. The device according to claim 22, wherein the plurality of nanoscale membranes includes membranes having different thicknesses, pore densities, and/or pore dimensions.

25. The device according to claim 1, wherein the nanoscale membrane has a pore density of between about $10^6$ and about $10^{12}$ per $cm^2$ of membrane.

26. The device according to claim 1, wherein the nanoscale membrane is between about 50 and about 100 nm thick.

27. The device according to claim 1, wherein the nanoscale membrane is between about 10 and about 50 nm thick.

28. The device according to claim 1, wherein the nanoscale membrane is less than about 10 nm thick.

29. The device according to claim 1, wherein the average diameter of the plurality of pores is between about 2 and 50 nanometers.

30. The device according to claim 1, wherein the nanoscale membrane is characterized by an area to thickness aspect ratio that is more than 10,000 to 1.

31. The device according to claim 1, wherein the semiconductor material is selected from the group of silicon, silicon alloys, p-doped silicon, and n-doped silicon.

32. The device according to claim 1, wherein the semiconductor material is in a crystalline form.

33. The device according to claim 1, wherein the nanoscale membrane comprises a cell surface receptor, an antibody, a ligand, a biological reagent, or a combination thereof, within the pores of said membrane.

34. The device according to claim 1 further comprising:
a power source electrically coupled to the nanoscale membrane in a manner effective to charge the membrane.

35. The device according to claim 34, wherein the nanoscale membrane is positively charged.

36. The device according to claim 34, wherein the nanoscale membrane is negatively charged.

37. A sterile package comprising:
a sealed package defining an interior that is sterile; and
a device according to claim 1 positioned within the interior of the sealed package.

38. A kit comprising the device according to claim 1 and one or more of (i) a cell culture medium, (ii) one or more cell lines, and (iii) instructions for co-culturing one or more cells.

39. The kit according to claim 38, wherein the device is sterile and positioned within a sealed package that defines a sterile environment.

40. A method of co-culturing two or more populations of cells comprising:
providing a device according to claim 1; and
culturing a first population of cells in a first chamber and a second population of cells in a second chamber.

41. The method according to claim 40, wherein said cells are physically separated yet are able to contact and/or communicate with each other through said plurality of pores.

42. The method according to claim 40, wherein said cells are able to communicate but not contact one another through said plurality of pores.

43. The method according to claim 40, wherein said populations of cells physically contact each other through said plurality of pores.

44. The method according to claim 40, wherein said population of cells are derived from an animal, bacteria, fungus, yeast, algae, and/or plant.

45. A method of visualizing cells comprising:
providing a cell culture device according to claim 1 with cells in the first and/or second chambers; and
observing the cells of the first and/or second chambers via microscopy.

46. The method according to claim 45 further comprising fixing the cells of the first and second chambers prior to said observing.

47. The method according to claim 45 further comprising staining and/or labeling cells prior to said observing.

48. The method according to claim 45, wherein said observing is carried out by light microscopy, Darkfield microscopy, Brightfield microscopy, differential interference contrast microscopy, phase contrast microscopy, polarized light microscopy, confocal microscopy, near-field scanning optical microscopy, fluorescence microscopy, scanning electron microscopy, or transmission electron microscopy.

49. A method of monitoring low abundance molecular species comprising:
providing a cell culture device according to claim 1 with cells in the first chamber; and
detecting the presence of low abundance molecular species in the second chamber.

50. The method according to claim 49 further comprising:
fixing the cells prior to said detecting.

51. The method according to claim 49 further comprising:
staining and/or labeling the low abundance molecular species or a detection reagent prior to said detecting.

* * * * *